United States Patent [19]

Hinman

[11] Patent Number: 4,540,764

[45] Date of Patent: Sep. 10, 1985

[54] REACTION PRODUCT OF TUNGSTEN CARBONYL/PYRROLIDINE COMPLEX WITH A FURAN ACID

[75] Inventor: P. Anthony Hinman, Torrance, Calif.

[73] Assignee: Hitco, Newport Beach, Calif.

[21] Appl. No.: 479,926

[22] Filed: Mar. 29, 1983

[51] Int. Cl.³ ............................................. C08G 79/00
[52] U.S. Cl. ...................................... 528/9; 528/271; 528/363; 528/395
[58] Field of Search ................... 528/9, 363, 395, 271

[56] References Cited

U.S. PATENT DOCUMENTS 4,185,043  1/1980  Shaffer ..................................... 528/9

Primary Examiner—Harold D. Anderson
Attorney, Agent, or Firm—Roylance, Abrams, Berdo & Goodman

[57] ABSTRACT

There are disclosed polymers containing tungsten chemically bonded in the polymer chain. The polymers are obtained by reacting 2-furanacrylic acid or 2-furoic acid with the reaction product of tungsten carbonyl with pyrrolidine. These polymers are useful as multi-cycle reimpregnation resins.

6 Claims, No Drawings

REACTION PRODUCT OF TUNGSTEN CARBONYL/PYRROLIDINE COMPLEX WITH A FURAN ACID

BACKGROUND OF THE INVENTION

This invention relates to thermosetting, solventless polymers containing variable ratios of tungsten to carbon atoms chemically bonded in the polymer chain which are particularly useful for multi-cycle reimpregnation of a carbon/carbon composite.

With the advent of aerospace products, carbon/carbon composites having high densities have come into widespread use. One or a combination of the following three methods for densification of carbon/carbon composites are commonly employed: (1) high temperature consolidation; (2) chemical vapor deposition: and (3) multi-cycle reimpregnation. For applications involving large parts or complex shapes, multicycle reimpregnation has been found to be the most effective method for imparting oxidation resistance and energy absorbing characteristics through the use of specifically formulated polymers.

A reimpregnation resin is a thermosetting polymer introduced as a liquid into the characteristic void of a carbon/carbon composite. The resin is subsequently cured and heat treated, thus increasing the density of the composite. Selected polymers impart specific desired characteristics to the composite depending upon the ultimate application. Viable reimpregnation resins must maintain a suitably low viscosity during the reimpregnation process and, in addition, exhibit a relatively high char yield. "Multi-cycle reimpregnation" is the term applied when the reimpregnation process is repeated a number of times.

U.S. Pat. No. 4,185,043 to Robert C. Shaffer discloses thermoplastic and thermosetting polymers which incorporate tungsten and/or molybdenum metal atoms. The metal atoms are incorporated into the polymer by reacting a monomer or polymer containing at least one free carboxyl group with a reaction product of tungsten or molybdenum carbonyl and pyrrolidine to obtain a polymer. It is disclosed that the polymers are useful as reimpregnation resins. However, the polymers disclosed in the above patent are not specifically designed for use as multi-cycle reimpregnation polymers.

SUMMARY OF THE INVENTION

It has now been discovered that suitable multi-cycle reimpregnation polymers may be prepared by reacting 2-furanacrylic acid or 2-furoic acid with the reaction product of tungsten carbonyl and pyrrolidine. The dark viscous polymer thus obtained may be utilized neat or it may be copolymerized with furfuryl alcohol or a dienophilic ester to obtain a variable metal content containing thermosetting multi-cycle reimpregnation resin. Because of the relatively low viscosity at moderate temperatures, the polymers of this invention may be used in a multi-cycle reimpregnation process without a solvent. Further, by appropriate choice of the amounts of reactants, precise variation in tungsten content is achieved while retaining the tungsten in atomic form in the polymer molecule. For maximum metal loading, the furan based polymr containing chemically bonded tungsten atoms in the polymer chain may be used neat in a multi-cycle reimpregnation process.

DESCRIPTION OF THE PREFERRED EMBODIMENTS

In order to prepare the polymers of this invention, a complex is first prepared by reacting tungsten carbonyl with pyrrolidine. The reaction between the tungsten carbonyl and pyrrolidine may be accomplished in one of several methods found in the literature, e.g., an article by Fowles et al entitled "The Reactions of Group VI Metal Carbonyls With Pyrrolidine, Piperazine and Morpholine", *Inorganic chemistry*, Vol. 3, No. 2, 1964, pages 257–259. The reaction product consisting of the pyrrolidine-tungsten carbonyl complex is ground to a fine powder for subsequent reaction. The reaction product of the pyrrolidine-tungsten carbonyl complex is believed to contain at least two moles of pyrrolidine to one mole of tungsten carbonyl.

The 2-furanacrylic acid or 2-furoic acid is reacted with the pyrrolidine-tungsten carbonyl reaction product by combining the two materials and heating the reaction mixture, preferably within the range of about 150° to 160° C. for from about two to four hours. The amount of pyrrolidine-tungsten carbonyl reaction product which is reacted with the acid may vary widely. Preferably, about two moles of acid are reacted per mole of pyrrolidine-tungsten carbonyl reaction product. The relatively low melting point of the furanacrylic acid and furoic acid permit the synthesis of high metal containing polymers without the use of solvents. This property, coupled with the relatively low viscosity and high char yield of the tungsten containing polymers render these polymers particularly suitable for multicycle reimpregnation polymers.

The polymers of this invention have the property of being both thermoplastic and thermosetting, i.e., at temperature of up to about 180° C. they are thermoplastic, i.e., they may be heated to obtain a low viscosity flowable material which, upon cooling, solidifies. At higher temperatures, i.e., above about 200° C., the materials are thermosetting, i.e., curable.

When it is desirable to obtain a lower amount of metal in the multi-cycle reimpregnation polymer, the polymers of this invention may be copolymerized with another material such as furfuryl alcohol or a dienophilic ester. The amount of metal in the finished resin may be controlled by the ratio of polymer of this invention to prepolymer used during the copolymerization process. Dienophilic prepolymers which may be polymerized with the tungsten containing polymers of this invention include polyester prepolymers prepared by recting an ethylenically unsaturated dicarboxylic acid or anhydride with a glycol.

The following examples illustrate the best mode contemplated for carrying out this invention.

EXAMPLE 1

One mole equivalent of tungsten hexacarbonyl and an excess of pyrrolidine are reacted to form the metal pyrrolidine complex. At the completion of the reaction, the product is washed and ground to a fine powder.

Two moles of 2-furanacrylic acid are added to one mole of the pyrrolidine-tungsten hexacarbonyl reaction product and the reagents are then heated to 150°–160° C. for approximately three hours. A clear, dark orange polymer results. This is a thermoplastic material which is solid at room temperature. It may be used as a multicycle reimpregnation resin in a carbon/carbon composite by heating it to melt it and then impregnating it into the void of a carbon/carbon composite. The polymer is then cured by heating at 210° C. for 40 hours. This cured thermoset resin, when subsequently carbonized at 800° C. for one hour, contains approximately 58% tungsten by weight.

EXAMPLE 2

Two moles of 2-furoic acid are heated until molten. One mole of the reaction product of tungsten hexacarbonyl and pyrrolidine obtained as described in Example 1 is added with constant stirring. The reactants are then heated to about 150° C. for two hours. A clear, dark, amber thermoplastic polymer results which is solid at room temperature. This polymer may be used as a multi-cycle reimpregnation polymer as described in Example 1.

The following example illustrates the copolymerization of a polymer of this invention with a dienophilic prepolymer, i.e., an ethylene glycol/maleic anhydride polyester prepolymer, in order to control the metal content of the resultant resin.

EXAMPLE 3

The polymer of Example 1, 496.00 g, is mixed with 143.52 g of furfuryl alcohol and heated to approximately 60° C. in a four liter reaction kettle. The kettle is then removed from the mantle and 328.00 g of a 2:1 molar ratio maleic anhydride/ethylene glycol prepolymer are mixed thoroughly with the reactants. The kettle is subsequently returned to the mantle and heated to approximately 150°–160° C. for a two hour period. The resulting product is a clear, dark, amber thermosetting resin which may be used as a multi-cycle reimpregnation resin for a carbon/carbon composite as previously described. When cured at 210° C. for 18 hours and subsequently carbonized at 800° C. for one hour, there is obtained a char containing approximately 26% tungsten by weight.

What is claimed is:

1. The thermoplastic/thermosetting reaction product of (1) 2-furanacrylic acid or 2-furoic acid and (2) a metal complex which is a reaction product of tungsten carbonyl with pyrrolidine, said product being a multi-cycle reimpregnation polymer.

2. The product as defined in claim 1 wherein (1) is 2-furanacrylic acid.

3. The product as defined in claim 1 wherein (1) is 2-furoic acid.

4. The product of claim 1 wherein two moles of (1) are reacted per mole of pyrrolidine-tungsten carbonyl reaction product.

5. The product of claim 2 wherein two moles of (1) are reacted per mole of pyrrolidine-tungsten carbonyl reaction product.

6. The product of claim 3 wherein two moles of (1) are reacted per mole of pyrrolidine-tungsten carbonyl reaction product.

* * * * *